US007723482B2

(12) United States Patent
Soulillou et al.

(10) Patent No.: US 7,723,482 B2
(45) Date of Patent: May 25, 2010

(54) ANTI-CD28 ANTIBODY

(75) Inventors: Jean-Paul Soulillou, Nantes (FR); Genevieve Laflamme, San Francisco, CA (US); Bernard Vanhove, Reze (FR); Daniel Olive, Marseilles (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 1419 days.

(21) Appl. No.: 10/450,832

(22) PCT Filed: Dec. 26, 2001

(86) PCT No.: PCT/FR01/04203

§ 371 (c)(1),
(2), (4) Date: Nov. 6, 2006

(87) PCT Pub. No.: WO02/051871

PCT Pub. Date: Jul. 4, 2002

(65) Prior Publication Data

US 2008/0038273 A1    Feb. 14, 2008

(30) Foreign Application Priority Data

Dec. 26, 2000    (FR) .................................. 00 17025

(51) Int. Cl.
C07K 16/00    (2006.01)
C07K 16/28    (2006.01)
C07K 16/46    (2006.01)
A61K 39/395    (2006.01)

(52) U.S. Cl. ............... 530/387.1; 530/387.3; 530/388.1; 530/388.22; 424/130.1; 424/133.1; 424/134.1; 424/141.1; 424/144.1

(58) Field of Classification Search ........................ None
See application file for complete search history.

(56) References Cited

U.S. PATENT DOCUMENTS 4,179,337 A    12/1979    Davis et al.
5,948,893 A    9/1999    June et al.

FOREIGN PATENT DOCUMENTS

EP    0 440 373    8/1991
WO    94 28912    12/1994

OTHER PUBLICATIONS

Nunes et al., International Immunology, 1993, 5: 311-315.*
Jennifer E. Woodward, et al., "T-Cell Alterations in Cardiac Allograft Recipients After B7 (CD80 and CD86) Blockade[1]", Transplantation, vol. 66, No. 1, Jul. 15, 1998, pp. 1-15.
Francesca Fallarino, et al., "B7-1 Engagement of Cytotoxic T Lymphocyte Antigen 4 Inhibits T Cell Activation in the Absence of CD28", J. Exp. Med., vol. 188, No. 1, Jul. 6, 1998, pp. 205-210.
Nitin K. Damle, et al., "Differential Regulatory Signals Delivered by Antibody Binding to the CD28 (Tp44) Molecule During the Activation of Human T Lymphocytes", The Journal of Immunology, vol. 140, No. 6, Mar. 1998, pp. 1753-1761.
Francoise Pages, et al., "Two Distinct Intracytoplasmic Regions of the T-cell Adhesion Molecule CD28 Participate in Phosphatidylinositol 3-Kinase Association", The Journal of Biological Chemistry, vol. 271, No. 16, Apr. 19, 1996, pp. 9403-9409.
Peter J. Perrin, et al., "Blockade of CD28 During In Vitro Activation of Encephalitogenic T Cells or After Disease Onset Ameliorates Experimental Autoimmune Encephalomyelitis[1]", The Journal of Immunology, vol. 163, 1999, pp. 1704-1710.
Tim Clackson, et al., "Making antibody fragments using phage display libraries", Letters to Nature, vol. 352, Aug. 15, 1991, pp. 624-628.
Edward G. Routledge, et al., "Reshaping antibodies for therapy", in protein Engineering go Antibody Molecules for Prophylactic and Therapeutic Applications in Man, 13-44, Academic Titles, Nottingham, England, 1993, pp. 1-48.
Michael A. Roguska, et al., "A comparison of two murine monoclonal antibodies humanized by CDR-grafting and variable domain resurfacing", Protein Engineering, vol. 9, No. 10, 1996, pp. 895-904.
P. Tan et al.: "Humanization of an anti-CD28 antibody using germline human antibody sequences" Blood, vol. 96, No. 11 Part 1, p. 31A Nov. 2000.
J. Nunes et al.: "CD28 mAbs with distinct binding properties differ in tehir ability to induce T cell activation: analysis of early and late activation events" International Immunology, vol. 5, No. 3, pp. 311-315, Mar. 1993.
L.K. Gilliland et al.: "Rapid and reliable cloning of antibody variable regions and generation of recombinant single chain antibody fragments" Tissue Antigens, vol. 47, No. 1, pp. 1-20, 1996.
Fabienne Haspot et al.: "Differential effect of DC28 versus B7 blockade on direct pathway of allorecegnition and self-restricted responses" Blood, vol. 99, No. 6, pp. 2228-2234, Mar. 15, 2002.

* cited by examiner

Primary Examiner—Ilia Ouspenski
(74) Attorney, Agent, or Firm—Oblon, Spivak, McClelland, Maier & Neustadt, L.L.P.

(57) ABSTRACT

An antibody or antibody fragment directed against the CD28 receptor which blocks the interaction between B7-1 or B7-2 and CD28. Methods for blocking activation via CD28, including CD28-dependent lymphocyte activation.

15 Claims, 5 Drawing Sheets

SEQUENCE LISTING

<160> NUMBER OF SEQ ID NOS: 4

<210> SEQ ID NO 1
<211> LENGTH: 732
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: CDS
<222> LOCATION: (1)..(732)

<400> SEQUENCE: 1

```
gtc aag ctg cag cag tca gga gct gag ctg gtg aaa ccc ggg gcg tcg      48
Val Lys Leu Gln Gln Ser Gly Ala Glu Leu Val Lys Pro Gly Ala Ser
1               5                   10                  15 gtg agg ctg tcc tgc aag gcg tct ggt tac acc ttc act gaa tat att      96
Val Arg Leu Ser Cys Lys Ala Ser Gly Tyr Thr Phe Thr Glu Tyr Ile
            20                  25                  30 ata cac tgg ata aag ctg agg tct gga cag ggt ctt gag tgg att ggg     144
Ile His Trp Ile Lys Leu Arg Ser Gly Gln Gly Leu Glu Trp Ile Gly
        35                  40                  45 tgg ttt tac cct gga agt aat gat ata cag tac aat gcg aaa ttc aag     192
Trp Phe Tyr Pro Gly Ser Asn Asp Ile Gln Tyr Asn Ala Lys Phe Lys
    50                  55                  60 ggc aag gcc aca ttg act gcg gac aaa tcc tcc agc acc gtc tat atg     240
Gly Lys Ala Thr Leu Thr Ala Asp Lys Ser Ser Ser Thr Val Tyr Met
65                  70                  75                  80 gaa ctt act gga ttg aca tct gag gac tct gcg gtc tat ttc tgt gca     288
Glu Leu Thr Gly Leu Thr Ser Glu Asp Ser Ala Val Tyr Phe Cys Ala
                85                  90                  95 aga cgc gac gat ttc tct ggt tac gac gcc ctt cct tac tgg ggc caa     336
Arg Arg Asp Asp Phe Ser Gly Tyr Asp Ala Leu Pro Tyr Trp Gly Gln
            100                 105                 110 ggg acc atg gtc acc gtc tcc tca ggt gga ggc ggt tca ggc gga ggt     384
Gly Thr Met Val Thr Val Ser Ser Gly Gly Gly Gly Ser Gly Gly Gly
        115                 120                 125 ggc tct ggc ggt ggc gga tcg gac atc cag atg acc cag tct cca gcc     432
Gly Ser Gly Gly Gly Gly Ser Asp Ile Gln Met Thr Gln Ser Pro Ala
    130                 135                 140 tcc cta tct gtt tct gtg gga gaa act gtc acc atc acg tgt cga aca     480
Ser Leu Ser Val Ser Val Gly Glu Thr Val Thr Ile Thr Cys Arg Thr
145                 150                 155                 160 aat gaa aat att tac agt aat tta gca tgg tat cag cag aaa cag gga     528
Asn Glu Asn Ile Tyr Ser Asn Leu Ala Trp Tyr Gln Gln Lys Gln Gly
                165                 170                 175 aaa tct cct cag ctc ctg atc tat gct gca aca cac tta gta gag ggt     576
Lys Ser Pro Gln Leu Leu Ile Tyr Ala Ala Thr His Leu Val Glu Gly
            180                 185                 190 gtg cca tca agg ttc agt ggc agt gga tca ggc aca cag tat tcc ctc     624
Val Pro Ser Arg Phe Ser Gly Ser Gly Ser Gly Thr Gln Tyr Ser Leu
        195                 200                 205 aag atc acc agc ctg cag tct gaa gat ttt ggg aat tat tac tgt caa     672
Lys Ile Thr Ser Leu Gln Ser Glu Asp Phe Gly Asn Tyr Tyr Cys Gln
    210                 215                 220 cac ttt tgg ggt act ccg tgc acg ttc gga ggg ggg acc aag ctg gaa     720
His Phe Trp Gly Thr Pro Cys Thr Phe Gly Gly Gly Thr Lys Leu Glu
225                 230                 235                 240 ata aaa cgg act                                                     732
Ile Lys Arg Thr
```

<210> SEQ ID NO 2
<211> LENGTH: 244
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 2

Val Lys Leu Gln Gln Ser Gly Ala Glu Leu Val Lys Pro Gly Ala Ser
1               5                   10                  15

Val Arg Leu Ser Cys Lys Ala Ser Gly Tyr Thr Phe Thr Glu Tyr Ile
            20                  25                  30

Ile His Trp Ile Lys Leu Arg Ser Gly Gln Gly Leu Glu Trp Ile Gly
        35                  40                  45

Trp Phe Tyr Pro Gly Ser Asn Asp Ile Gln Tyr Asn Ala Lys Phe Lys
    50                  55                  60

Gly Lys Ala Thr Leu Thr Ala Asp Lys Ser Ser Thr Val Tyr Met
65                  70                  75                  80

Glu Leu Thr Gly Leu Thr Ser Glu Asp Ser Ala Val Tyr Phe Cys Ala
                85                  90                  95

Arg Arg Asp Asp Phe Ser Gly Tyr Asp Ala Leu Pro Tyr Trp Gly Gln
            100                 105                 110

Gly Thr Met Val Thr Val Ser Ser Gly Gly Gly Ser Gly Gly Gly
        115                 120                 125

Gly Ser Gly Gly Gly Ser Asp Ile Gln Met Thr Gln Ser Pro Ala
    130                 135                 140

Ser Leu Ser Val Ser Val Gly Glu Thr Val Thr Ile Thr Cys Arg Thr
145                 150                 155                 160

Asn Glu Asn Ile Tyr Ser Asn Leu Ala Trp Tyr Gln Gln Lys Gln Gly
                165                 170                 175

Lys Ser Pro Gln Leu Leu Ile Tyr Ala Ala Thr His Leu Val Glu Gly
            180                 185                 190

Val Pro Ser Arg Phe Ser Gly Ser Gly Ser Gly Thr Gln Tyr Ser Leu
        195                 200                 205

Lys Ile Thr Ser Leu Gln Ser Glu Asp Phe Gly Asn Tyr Tyr Cys Gln
    210                 215                 220

His Phe Trp Gly Thr Pro Cys Thr Phe Gly Gly Thr Lys Leu Glu
225                 230                 235                 240

Ile Lys Arg Thr

<210> SEQ ID NO 3
<211> LENGTH: 2013
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: CDS
<222> LOCATION: (1)..(2013)

<400> SEQUENCE: 3 atg aaa aag aca gct atc gcg att gca gtg gca ctg gct ggt ttc gct        48
Met Lys Lys Thr Ala Ile Ala Ile Ala Val Ala Leu Ala Gly Phe Ala
1               5                   10                  15 acc gta gcg cag gcc gac tac aaa gat atc gtc aag ctg cag cag tca        96
Thr Val Ala Gln Ala Asp Tyr Lys Asp Ile Val Lys Leu Gln Gln Ser
            20                  25                  30

```
gga gct gag ctg gtg aaa ccc ggg gcg tcg gtg agg ctg tcc tgc aag      144
Gly Ala Glu Leu Val Lys Pro Gly Ala Ser Val Arg Leu Ser Cys Lys
         35                  40                  45 gcg tct ggt tac acc ttc act gaa tat att ata cac tgg ata aag ctg      192
Ala Ser Gly Tyr Thr Phe Thr Glu Tyr Ile Ile His Trp Ile Lys Leu
 50                  55                  60 agg tct gga cag ggt ctt gag tgg att ggg tgg ttt tac cct gga agt      240
Arg Ser Gly Gln Gly Leu Glu Trp Ile Gly Trp Phe Tyr Pro Gly Ser
65                  70                  75                  80 aat gat ata cag tac aat gcg aaa ttc aag ggc aag gcc aca ttg act      288
Asn Asp Ile Gln Tyr Asn Ala Lys Phe Lys Gly Lys Ala Thr Leu Thr
                 85                  90                  95 gcg gac aaa tcc tcc agc acc gtc tat atg gaa ctt act gga ttg aca      336
Ala Asp Lys Ser Ser Ser Thr Val Tyr Met Glu Leu Thr Gly Leu Thr
            100                 105                 110 tct gag gac tct gcg gtc tat ttc tgt gca aga cgc gac gat ttc tct      384
Ser Glu Asp Ser Ala Val Tyr Phe Cys Ala Arg Arg Asp Asp Phe Ser
        115                 120                 125 ggt tac gac gcc ctt cct tac tgg ggc caa ggg acc atg gtc acc gtc      432
Gly Tyr Asp Ala Leu Pro Tyr Trp Gly Gln Gly Thr Met Val Thr Val
130                 135                 140 tcc tca ggt gga ggc ggt tca ggc gga ggt ggc tct ggc ggt ggc gga      480
Ser Ser Gly Gly Gly Gly Ser Gly Gly Gly Gly Ser Gly Gly Gly Gly
145                 150                 155                 160 tcg gac atc cag atg acc cag tct cca gcc tcc cta tct gtt tct gtg      528
Ser Asp Ile Gln Met Thr Gln Ser Pro Ala Ser Leu Ser Val Ser Val
                165                 170                 175 gga gaa act gtc acc atc acg tgt cga aca aat gaa aat att tac agt      576
Gly Glu Thr Val Thr Ile Thr Cys Arg Thr Asn Glu Asn Ile Tyr Ser
            180                 185                 190 aat tta gca tgg tat cag cag aaa cag gga aaa tct cct cag ctc ctg      624
Asn Leu Ala Trp Tyr Gln Gln Lys Gln Gly Lys Ser Pro Gln Leu Leu
        195                 200                 205 atc tat gct gca aca cac tta gta gag ggt gtg cca tca agg ttc agt      672
Ile Tyr Ala Ala Thr His Leu Val Glu Gly Val Pro Ser Arg Phe Ser
210                 215                 220 ggc agt gga tca ggc aca cag tat tcc ctc aag atc acc agc ctg cag      720
Gly Ser Gly Ser Gly Thr Gln Tyr Ser Leu Lys Ile Thr Ser Leu Gln
225                 230                 235                 240 tct gaa gat ttt ggg aat tat tac tgt caa cac ttt tgg ggt act ccg      768
Ser Glu Asp Phe Gly Asn Tyr Tyr Cys Gln His Phe Trp Gly Thr Pro
                245                 250                 255 tgc acg ttc gga ggg ggg acc aag ctg gaa ata aaa cgg act gtg gct      816
Cys Thr Phe Gly Gly Gly Thr Lys Leu Glu Ile Lys Arg Thr Val Ala
            260                 265                 270 gca cca tct gaa ttc aac aag atc acc ccc aac ctg gct gag ttc gcc      864
Ala Pro Ser Glu Phe Asn Lys Ile Thr Pro Asn Leu Ala Glu Phe Ala
        275                 280                 285 ttc agc cta tac cgc cag ctg gca cac agt cca aac agc acc aat atc      912
Phe Ser Leu Tyr Arg Gln Leu Ala His Gln Ser Asn Ser Thr Asn Ile
290                 295                 300 ttc ttc tcc cca gtg agc atc gct aca gcc ttt gca atg ctc tcc ctg      960
Phe Phe Ser Pro Val Ser Ile Ala Thr Ala Phe Ala Met Leu Ser Leu
305                 310                 315                 320 ggg acc aag gct gac act cac gat gaa atc ctg gag ggc ctg aat ttc     1008
Gly Thr Lys Ala Asp Thr His Asp Glu Ile Leu Glu Gly Leu Asn Phe
                325                 330                 335 aac ctc acg gag att ccg gag gct cag atc cat gaa ggc ttc cag gaa     1056
Asn Leu Thr Glu Ile Pro Glu Ala Gln Ile His Glu Gly Phe Gln Glu
            340                 345                 350
```

-continued

```
ctc ctc cgt acc ctc aac cag cca gac agc cag ctc cag ctg acc acc       1104
Leu Leu Arg Thr Leu Asn Gln Pro Asp Ser Gln Leu Gln Leu Thr Thr
        355                 360                 365 ggc aat ggc ctg ttc ctc agc gag ggc ctg aag cta gtg gat aag ttt       1152
Gly Asn Gly Leu Phe Leu Ser Glu Gly Leu Lys Leu Val Asp Lys Phe
370                 375                 380 ttg gag gat gtt aaa aag ttg tac cac tca gaa gcc ttc act gtc aac       1200
Leu Glu Asp Val Lys Lys Leu Tyr His Ser Glu Ala Phe Thr Val Asn
385                 390                 395                 400 ttc ggg gac acc gaa gag gcc aag aaa cag atc aac gat tac gtg gag       1248
Phe Gly Asp Thr Glu Glu Ala Lys Lys Gln Ile Asn Asp Tyr Val Glu
            405                 410                 415 aag ggt act caa ggg aaa att gtg gat ttg gtc aag gag ctt gac aga       1296
Lys Gly Thr Gln Gly Lys Ile Val Asp Leu Val Lys Glu Leu Asp Arg
        420                 425                 430 gac aca gtt ttt gct ctg gtg aat tac atc ttc ttt aaa ggc aaa tgg       1344
Asp Thr Val Phe Ala Leu Val Asn Tyr Ile Phe Phe Lys Gly Lys Trp
            435                 440                 445 gag aga ccc ttt gaa gtc aag gac acc gag gaa gag gac ttc cac gtg       1392
Glu Arg Pro Phe Glu Val Lys Asp Thr Glu Glu Glu Asp Phe His Val
450                 455                 460 gac gag gtg acc acc gtg aag gtg cct atg atg aag cgt tta ggc atg       1440
Asp Glu Val Thr Thr Val Lys Val Pro Met Met Lys Arg Leu Gly Met
465                 470                 475                 480 ttt aac atc cag cac tgt aag aag ctg tcc agc tgg gtg ctg ctg atg       1488
Phe Asn Ile Gln His Cys Lys Lys Leu Ser Ser Trp Val Leu Leu Met
            485                 490                 495 aaa tac ctg ggc aat gcc acc gcc atc ttc ttc ctg cct gat gag ggg       1536
Lys Tyr Leu Gly Asn Ala Thr Ala Ile Phe Phe Leu Pro Asp Glu Gly
        500                 505                 510 aaa cta cag cac ctg gaa aat gaa ctc acc cac gat atc atc acc aag       1584
Lys Leu Gln His Leu Glu Asn Glu Leu Thr His Asp Ile Ile Thr Lys
        515                 520                 525 ttc ctg gaa aat gaa gac aga agg tct gcc agc tta cat tta ccc aaa       1632
Phe Leu Glu Asn Glu Asp Arg Arg Ser Ala Ser Leu His Leu Pro Lys
530                 535                 540 ctg tcc att act gga acc tat gat ctg aag agc gtc ctg ggt caa ctg       1680
Leu Ser Ile Thr Gly Thr Tyr Asp Leu Lys Ser Val Leu Gly Gln Leu
545                 550                 555                 560 ggc atc act aag gtc ttc agc aat ggg gct gac ctc tcc ggg gtc aca       1728
Gly Ile Thr Lys Val Phe Ser Asn Gly Ala Asp Leu Ser Gly Val Thr
            565                 570                 575 gag gag gca ccc ctg aag ctc tcc aag gcc gtg cat aag gct gtg ctg       1776
Glu Glu Ala Pro Leu Lys Leu Ser Lys Ala Val His Lys Ala Val Leu
        580                 585                 590 acc atc gac gag aaa ggg act gaa gct gct ggg gcc atg ttt tta gag       1824
Thr Ile Asp Glu Lys Gly Thr Glu Ala Ala Gly Ala Met Phe Leu Glu
        595                 600                 605 gcc ata ccc atg tct atc ccc ccc gag gtc aag ttc aac aaa ccc ttt       1872
Ala Ile Pro Met Ser Ile Pro Pro Glu Val Lys Phe Asn Lys Pro Phe
            610                 615                 620 gtc ttc tta atg att gaa caa aat acc aag tct ccc ctc ttc atg gga       1920
Val Phe Leu Met Ile Glu Gln Asn Thr Lys Ser Pro Leu Phe Met Gly
625                 630                 635                 640 aaa gtg gtg aat ccc acc caa aaa ctc gag gga gaa ttc gaa cag aaa       1968
Lys Val Val Asn Pro Thr Gln Lys Leu Glu Gly Glu Phe Glu Gln Lys
            645                 650                 655 ctg atc tct gaa gaa gac ctg aac cac cac cac cac cac tga taa           2013
Leu Ile Ser Glu Glu Asp Leu Asn His His His His His
        660                 665
```

<210> SEQ ID NO 4
<211> LENGTH: 669
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 4

```
Met Lys Lys Thr Ala Ile Ala Ile Ala Val Ala Leu Ala Gly Phe Ala
1               5                   10                  15

Thr Val Ala Gln Ala Asp Tyr Lys Asp Ile Val Lys Leu Gln Gln Ser
            20                  25                  30

Gly Ala Glu Leu Val Lys Pro Gly Ala Ser Val Arg Leu Ser Cys Lys
        35                  40                  45

Ala Ser Gly Tyr Thr Phe Thr Glu Tyr Ile Ile His Trp Ile Lys Leu
    50                  55                  60

Arg Ser Gly Gln Gly Leu Glu Trp Ile Gly Trp Phe Tyr Pro Gly Ser
65                  70                  75                  80

Asn Asp Ile Gln Tyr Asn Ala Lys Phe Lys Gly Lys Ala Thr Leu Thr
                85                  90                  95

Ala Asp Lys Ser Ser Thr Val Tyr Met Glu Leu Thr Gly Leu Thr
            100                 105                 110

Ser Glu Asp Ser Ala Val Tyr Phe Cys Ala Arg Arg Asp Asp Phe Ser
        115                 120                 125

Gly Tyr Asp Ala Leu Pro Tyr Trp Gly Gln Gly Thr Met Val Thr Val
    130                 135                 140

Ser Ser Gly Gly Gly Gly Ser Gly Gly Gly Gly Ser Gly Gly Gly Gly
145                 150                 155                 160

Ser Asp Ile Gln Met Thr Gln Ser Pro Ala Ser Leu Ser Val Ser Val
                165                 170                 175

Gly Glu Thr Val Thr Ile Thr Cys Arg Thr Asn Glu Asn Ile Tyr Ser
            180                 185                 190

Asn Leu Ala Trp Tyr Gln Gln Lys Gln Gly Lys Ser Pro Gln Leu Leu
        195                 200                 205

Ile Tyr Ala Ala Thr His Leu Val Glu Gly Val Pro Ser Arg Phe Ser
    210                 215                 220

Gly Ser Gly Ser Gly Thr Gln Tyr Ser Leu Lys Ile Thr Ser Leu Gln
225                 230                 235                 240

Ser Glu Asp Phe Gly Asn Tyr Tyr Cys Gln His Phe Trp Gly Thr Pro
                245                 250                 255

Cys Thr Phe Gly Gly Gly Thr Lys Leu Glu Ile Lys Arg Thr Val Ala
            260                 265                 270

Ala Pro Ser Glu Phe Asn Lys Ile Thr Pro Asn Leu Ala Glu Phe Ala
        275                 280                 285

Phe Ser Leu Tyr Arg Gln Leu Ala His Gln Ser Asn Ser Thr Asn Ile
    290                 295                 300

Phe Phe Ser Pro Val Ser Ile Ala Thr Ala Phe Ala Met Leu Ser Leu
305                 310                 315                 320
```

-continued

```
Gly Thr Lys Ala Asp Thr His Asp Glu Ile Leu Gly Leu Asn Phe
            325                 330                 335

Asn Leu Thr Glu Ile Pro Glu Ala Gln Ile His Glu Gly Phe Gln Glu
            340                 345                 350

Leu Leu Arg Thr Leu Asn Gln Pro Asp Ser Gln Leu Gln Leu Thr Thr
            355                 360                 365

Gly Asn Gly Leu Phe Leu Ser Glu Gly Leu Lys Leu Val Asp Lys Phe
            370                 375                 380

Leu Glu Asp Val Lys Lys Leu Tyr His Ser Glu Ala Phe Thr Val Asn
385                 390                 395                 400

Phe Gly Asp Thr Glu Glu Ala Lys Lys Gln Ile Asn Asp Tyr Val Glu
                    405                 410                 415

Lys Gly Thr Gln Gly Lys Ile Val Asp Leu Val Lys Glu Leu Asp Arg
                    420                 425                 430

Asp Thr Val Phe Ala Leu Val Asn Tyr Ile Phe Phe Lys Gly Lys Trp
                    435                 440                 445

Glu Arg Pro Phe Glu Val Lys Asp Thr Glu Glu Asp Phe His Val
            450                 455                 460

Asp Glu Val Thr Thr Val Lys Val Pro Met Met Lys Arg Leu Gly Met
465                 470                 475                 480

Phe Asn Ile Gln His Cys Lys Lys Leu Ser Ser Trp Val Leu Leu Met
                    485                 490                 495

Lys Tyr Leu Gly Asn Ala Thr Ala Ile Phe Phe Leu Pro Asp Glu Gly
                    500                 505                 510

Lys Leu Gln His Leu Glu Asn Glu Leu Thr His Asp Ile Ile Thr Lys
                    515                 520                 525

Phe Leu Glu Asn Glu Asp Arg Arg Ser Ala Ser Leu His Leu Pro Lys
            530                 535                 540

Leu Ser Ile Thr Gly Thr Tyr Asp Leu Lys Ser Val Leu Gly Gln Leu
545                 550                 555                 560

Gly Ile Thr Lys Val Phe Ser Asn Gly Ala Asp Leu Ser Gly Val Thr
                    565                 570                 575

Glu Glu Ala Pro Leu Lys Leu Ser Lys Ala Val His Lys Ala Val Leu
            580                 585                 590

Thr Ile Asp Glu Lys Gly Thr Glu Ala Ala Gly Ala Met Phe Leu Glu
            595                 600                 605

Ala Ile Pro Met Ser Ile Pro Pro Glu Val Lys Phe Asn Lys Pro Phe
            610                 615                 620

Val Phe Leu Met Ile Glu Gln Asn Thr Lys Ser Pro Leu Phe Met Gly
625                 630                 635                 640

Lys Val Val Asn Pro Thr Gln Lys Leu Glu Gly Glu Phe Glu Gln Lys
                    645                 650                 655

Leu Ile Ser Glu Glu Asp Leu Asn His His His His
            660                 665
```

ANTI-CD28 ANTIBODY

BACKGROUND OF THE INVENTION

1. Field of the Invention

The invention relates to antibodies directed against the CD28 lymphocyte receptor and to their fragments, and to their therapeutic uses, in particular in the context of regulating T cell activation.

2. Description of the Related Art

Abnormal activation of T cells is involved in the pathogenesis of many autoimmune diseases, and also in transplant rejection phenomena, where they cause an immune response directed against the transplanted organ to develop.

T lymphocyte activation requires an activating signal, induced by the recognition, by T receptors (TCRs) of the antigen associated with the class II major histocompatibility complex (MHC) and presented by antigen-presenting cells (APCs). However, this activation only causes proliferation of T cells and secretion of specific immunomodulatory cytokines (such as interleukin 2, gamma interferon or interleukin 4) if other T co-stimulation systems are also activated.

One of the most important systems for regulating T lymphocyte activation is the molecular system B7/CD28/CTLA4. This system plays, for example, an essential role in the mechanisms of transplant rejection [Woodward et al., Transplantation, 66, 14-20, (1998)]. The molecules B7.1 (CD80) and B7.2 (CD86) borne by the APCs can activate the CD28 receptor and also the CTLA4 receptor of T lymphocytes. The activation of CD28 sends the T lymphocyte a positive signal which stimulates the cell; on the other hand, the activation of CTLA4 sends a negative signal which leads to a non-response (anergy) [FALLARINO et al., J. Exp. Med., 188, 205-210, (1998)].

Dormant T lymphocytes express a large amount of CD28 and very little CTLA4. When there is a first cognitive contact between an APC and a T lymphocyte, the CD28/B7 interaction is favored, which activates the cell. It is only several hours after the initiation of activation that, due to the increase in membrane expression of CTLA4, the affinity of which for B7 is 5 to 10 times greater than that of CD28, the B7/CD28 interaction shifts in favor of a B7/CTLA4 interaction.

Currently, cyclosporin is mainly used to block T lymphocyte activation, in particular in the context of organ transplants. Despite the effectiveness of this medicinal product, it does not, however, confer absolute protection. In addition, it acts by blocking all the calcium-dependent cell activation pathways, and therefore has a biological activity which is not strictly T lyphocyte specific and leads to a considerable number of side effects. It is therefore desirable to develop new immunosuppressants which have a defined method of action and greater specificity.

It has been postulated that selective inhibition of the agonist signal given to the T cell by CD28, leaving the antagonist system consisting of the pair CTLA4/B7 intact, via specific blocking of the CD28/B7 interaction, would make it possible to prevent T lymphocyte activation. Such specific blocking of the CD28/B7 interaction can be obtained using an antibody directed against CD28.

BRIEF SUMMARY OF THE INVENTION

Anti-CD28 antibodies capable of preventing CD28 binding to B7 are known. However, they have the drawback, when they are used in their divalent native form, of bringing about the dimerization and the activation of CD28 via their binding with this receptor. However, monovalent fragments derived from these antibodies are capable of blocking the CD28 receptor without activating it [DAMLE et al., J. Immunol. 140, 1753-1761, (1988); NUNES et al., Int. Immunol., 5, 311-315 (1993); PAGES et al., J. Biol. Chem., 271, 9403, (1996)].

It has thus been reported [PERRIN et al., J. Immunol. 163, 1704-1710, (1999)] that Fab fragments derived from an anti-CD28 antibody can curb the clinical symptoms of experimental autoimmune encephalitis induced in mice by the administration of myelin or the transfer of T cells from an affected animal.

Monovalent Fab or scFv fragments derived from an anti-CD28 antibody can potentially be used to prevent T lymphocyte activation via specific blocking of the CD28/B7 interaction.

Fab fragments result from the action of papain on an immunoglobulin molecule, and each contain a light chain and the first half of a heavy chain; scfv fragments consist of the variable portions of the heavy and light chains of an antibody, connected to one another via a flexible linker [CLACKSON et al., Nature, 352, 624-628, (1991)], thus forming a single-chain protein.

These monovalent fragments frequently exhibit less affinity for the antigen than the native antibodies, which can limit their possibilities for use in diagnostic or therapeutic applications.

The inventors have succeeded in selecting, among various antibodies which recognize the CD28 antigen, an antibody capable of blocking the CD28/B7 interaction, the monovalent fragments of which exhibit sufficient affinity for the antigen so that they can be used, in vitro or in vivo, to block the CD28 receptor without activation of this receptor.

This antibody, called CD28.3, is produced by the hybridoma deposited, according to the terms of the Treaty of Budapest, on Nov. 28, 2000, with the CNCM (Collection Nationale de Cultures de Microorganismes [National Collection of Cultures and Microorganisms], 25 rue du Docteur Roux, 75724 PARIS CEDEX 15), under the number I-2582.

A subject of the present invention is a protein capable of binding specifically to the CD28 lymphocyte receptor and of blocking the CD28/B7 interaction, characterized in that it comprises at least the CDRs of the heavy chain and of the light chain of the immunoglobulin CD28.3.

DETAILED DESCRIPTION OF THE INVENTION

CDRs (complementarity determining regions) are the portions of the variable regions of an immunoglobulin which are involved in antigen recognition specificity.

Proteins in accordance with the invention thus encompass in particular:
a) the antibody CD28.3 produced by the hybridoma CNCM I-2582;
b) the Fv, Fab, Fab'2 or scfv fragments of the antibody CD28.3;
c) the chimeric or humanized antibodies obtained from the variable regions of CD28.3;
d) the fragments of the antibodies b) above comprising the CDRs of the antibody CD28.3, with a monovalent Fv, Fab or scfv fragments, or divalent Fab'2 fragments;
e) the recombinant proteins comprising a fragment b) or d) and a heterologous polypeptide.

They may, for example, be:
divalent or plurivalent derivatives of scfv fragments, such as "diabodies" or "triabodies", resulting from the association of 2 or 3 scFv fragments;
proteins combining at least one antibody fragment comprising the CDRs of the antibody CD28.3, with at least one antibody fragment comprising the CDRs of an antibody of different specificity; by way of examples, mention will be made of bispecific immunoglobulins, conjugates of an Fv or Fab fragment containing the CDRs of CD28.3 with an Fv or Fab fragment of an antibody of different specificity, and "bispecific diabodies" resulting from the association of an scFv fragment containing the CDRs of CD28.3 with an Fv or Fab fragment of an antibody of different specificity;
proteins combining at least one antibody fragment comprising the CDRs of the antibody CD28.3, with a molecule having pharmacological activity (for example a toxin) or effector properties (for example an Fc fragment);
proteins combining at least one antibody fragment comprising the CDRs of the antibody CD28.3, with a molecule which makes it possible to prolong its plasma halflife when it is administered in vivo; it is, for example, possible to combine said antibody fragment with a water-soluble polypeptide of sufficient molecular mass for the molecular mass of the fusion polypeptide thus obtained to be greater than the renal filtration threshold. In this case, a polypeptide will be chosen which, unlike Fc fragments, cannot associate as dimers, and which does not have its own effector activity liable to cause unfortunate side effects. Polypeptides which have these properties can advantageously be obtained from water-soluble serum proteins, namely, in particular, serum albumin, haptoglobulin, ITIH2 (inter-alpha (globulin) inhibitor, H2 polypeptide), transferrin, CBG (corticosteroid binding globulin), α1-antitrypsin, ITIH4 (inter-alpha (globulin) inhibitor, H4 polypeptide), AACT (alpha-1-antichymotrypsin), TBG (thyroxine binding globulin), fibrinogen and prothrombin, in order to prepare fusion proteins with scFv fragments derived from anti-CD28 antibodies. It is also possible to conjugate a protein in accordance with the invention with a polyol, for example polyethylene glycol, as described, for example, in U.S. Pat. No. 4,179,337.

Figure 1:
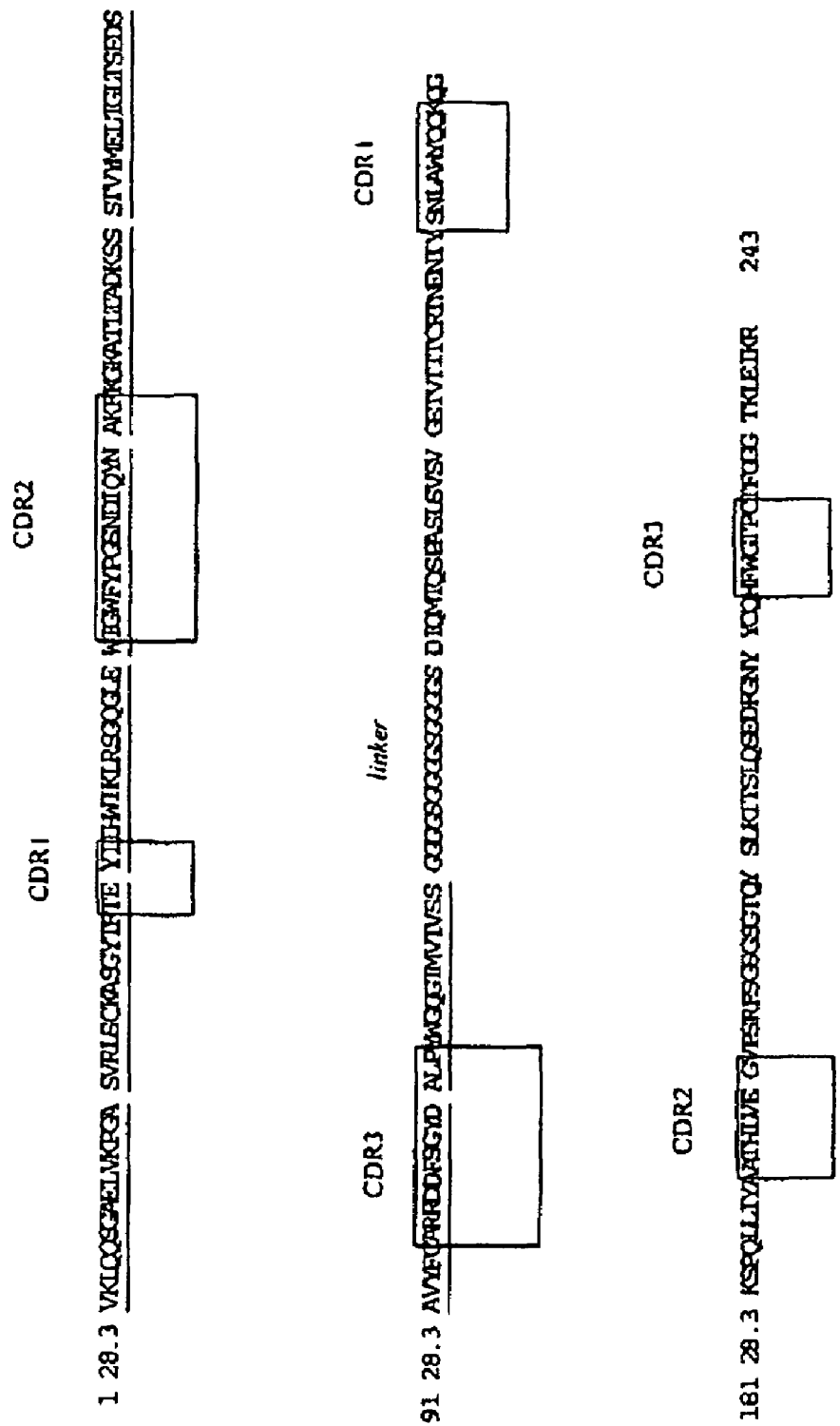
FIG. 1 illustrates an example of a protein in accordance with the invention, which represents an scFv fragment derived from the antibody CD28.3. The sequences of the CDRs of the antibody CD28.3 are boxed in the sequence represented in FIG. 1.

An example of a protein in accordance with the invention is illustrated in FIG. 1, which represents an scFv fragment derived from the antibody CD28.3. The sequences of the CDRs of the antibody CD28.3 are boxed in the sequence represented in FIG. 1.

The nucleotide sequence encoding this scFv fragment is represented in the attached sequence listing under the number SEQ ID No. 1, and the corresponding peptide sequence is represented under the number SEQ ID No. 2.

Fv, Fab or Fab'2 fragments in accordance with the invention can be obtained by the conventional techniques of enzyme digestion, from the antibody CD28.3.

A plasmid containing a polynucleotide encoding an scFv fragment of CD28.3, fused to a polynucleotide encoding amino acids 53 to 425 of α1-antitrypsin was deposited, according to the terms of the Treaty of Budapest, on Dec. 11, 2001, with the CNCM (Collection Nationale de Cultures de Microorganismes [National Collection of Cultures and Microorganisms], 25 rue du Docteur Roux, 75724 PARIS CEDEX 15), under the number I-2762.

Proteins in accordance with the invention such as chimeric or recombinant antibodies, scFv fragments and their derivatives, etc., can be obtained by conventional genetic engineering techniques, such as those described by SAMBROOK et al. [MOLECULAR CLONING, A LABORATORY MANUAL, 2nd Ed., Cold Spring Harbor Laboratory Press, Cold Spring Harbor, N.Y., (1989)].

Polynucleotides encoding the variable regions of the anti-CD28.3 antibody can, for example, be obtained by cloning said variable regions from a cDNA library of the hybridoma CD28.3, or from the plasmid CNCM I-2762. They can also be prepared, completely or partially, by nucleic acid synthesis, based on the nucleotide sequences of said variable regions. It is, for example, possible to synthesize polynucleotides encoding the CDRs of CD28.3, and to incorporate them into the framework regions (FRs) of another antibody, in particular of an antibody of human origin, using techniques, known in themselves, of CDR grafting, such as those described by ROUTLEDGE et al. ["Reshaping antibodies for therapy", in Protein Engineering of Antibody Molecules for Prophylactic and Therapeutic Applications in Man, 13-44, Academic Titles, Nottingham, England (1993)] or by ROGUSKA et al. Protein Engineering, 9(10), 895-904, (1996)].

A subject of the present invention is also any nucleic acid molecule encoding a protein in accordance with the invention comprising the CDRs of the antibody CD28.3, and also any recombinant vector, in particular any expression vector, comprising said nucleic acid molecule.

A subject of the present invention is also any cell expressing a protein in accordance with the invention comprising the CDRs of the antibody CD28.3. This encompasses in particular the hybridoma CNCM I-2582, and also the host cells transformed with a nucleic acid molecule in accordance with the invention.

Nucleic acid molecules in accordance with the invention may advantageously comprise, besides a sequence encoding a protein in accordance with the invention, a sequence encoding a signal peptide allowing secretion of said protein; they may also comprise one or more sequence(s) encoding one or more marker peptide(s) for detecting, and/or facilitating the purification of, said protein.

Expression vectors in accordance with the invention comprise at least one nucleic acid sequence encoding a protein in accordance with the invention, associated with transcription—and translation-controlling elements which are active in the host cell chosen. Vectors which can be used to construct expression vectors in accordance with the invention are known in themselves, and will be chosen in particular as a function of the host cell intended to be used.

Host cells which can be used in the context of the present invention can be prokaryotic or eukaryotic cells. Among the eukaryotic cells which can be used, mention will in particular be made of plant cells, cells from yeast, such as *Saccharomyces*, insect cells, such as *Drosophila* or *Spodoptera* cells, and mammalian cells such as HeLa, CHO, 3T3, C127, BHK, COS, etc., cells.

The construction of expression vectors in accordance with the invention and the transformation of the host cells can be carried out by the conventional techniques of molecular biology.

A subject of the invention is also a method for producing a protein in accordance with the invention, characterized in that it comprises culturing at least one cell in accordance with the invention, and recovering said protein from said culture.

If the protein is secreted, it can be recovered directly from the culture medium; if not, cell lysis will be carried out beforehand.

The protein can then be purified from the culture medium or from the cell lysate, by conventional procedures, known in themselves to those skilled in the art, for example by fractionated precipitation, in particular precipitation with ammonium sulfate, electrophoresis, gel filtration, affinity chromatography, etc.

The proteins in accordance with the invention can be used, in vitro, to study the proliferative response or the differentiation of T lymphocytes responding to an antigenic, viral, allogenic or xenogenic stimulation. They can also be used, in vitro, to induce the differentiation of T lymphocytes taken from a patient, for example the induction of tolerance with respect to an antigen or to an alloantigen, intended to be subsequently re-administered in vivo.

They may also be used to obtain medicinal products, or diagnostic reagents.

Proteins in accordance with the invention which are divalent, i.e. which have 2 CD28 receptor-binding sites, and thus capable of inducing dimerization of this receptor, can be used in all situations where it is desired to activate this CD28 receptor, i.e. to increase the response of a T lymphocyte with respect to an antigen.

Proteins in accordance with the invention which are monovalent, i.e. which have a single CD28 receptor-binding site, can be used in all situations where it is desired to selectively block this receptor without activating it, in order to induce immunosuppression.

A protein in accordance with the invention, comprising a monovalent fragment derived from an anti-CD28 antibody, can in particular be used to obtain an immunosuppressant medicinal product which selectively blocks T cell activation phenomena involving the CD28 receptor, and which does not have the drawbacks of known immunosuppressants such as cyclosporin.

The T immunosuppression by selective blocking of CD28 with protein in accordance with the invention has applications in all T lymphocyte-dependent pathological conditions.

These are essentially transplant rejection, graft-versus-host disease, T lymphocyte-mediated autoimmune diseases, such as type I diabetes or multiple sclerosis, and type IV hypersensitivity, which is involved in allergic phenomena and also in the pathogenesis of chronic inflammatory diseases following infection with a pathogenic agent (in particular leprosy, tuberculosis, leishmaniasis, listeriosis, etc.).

The present invention will be understood more clearly from the further description which follows, which refers to nonlimiting examples of preparation and of use of antibodies in accordance with the invention.

EXAMPLE 1

Choice of an Antibody Producing Monovalent Fragments, Properties of Monovalent Fab Fragments Derived from CD28.3

Some of the properties of several anti-CD28 antibodies (CD28.1, CD28.2, CD28.3, CD28.4, CD28.5 and CD28.6) are described in the publication by NUNES et al. [Int. Immunol., 5, 311, (1993)]. These various antibodies, which are not accessible to the public, were provided by the laboratory of Daniel OLIVE (INSERM). The antigen-binding properties of the monovalent Fab fragments of these various antibodies were compared.

5 mg of Fab fragments of each of these antibodies were prepared by digestion with papain (papain/antibody molar ratio=1/100) for 24 hours at 37° C., followed by inactivation of the enzyme with 0.03M iodoacetamide, and dialysis against PBS to remove the iodoacetamide.

1) Binding of the Fab Fragments to CD28+ Jurkat T Cells:

100,000 CD28+ Jurkat cells in 100 µl are incubated in PBS-1% BSA-0.1% $NaN_3$ at 4° C. for 30 minutes with increasing concentrations of anti-CD28 antibodies or of their Fab fragments. After washing, the cells are incubated in a similar way with an FITC-conjugated anti-mouse IgG goat antibody, washed, and analyzed by cytofluorometry.

Figure 2:
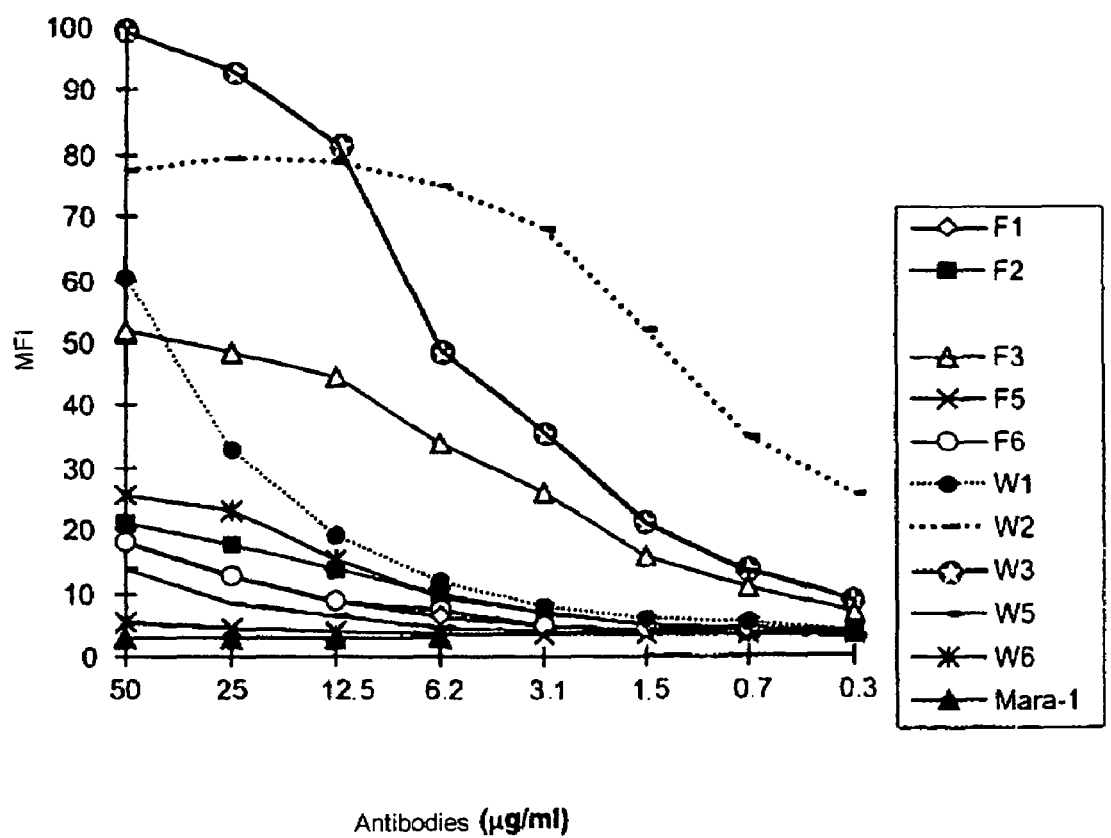
FIG. 2 shows the results of binding of the Fab fragments to CD28+Jurkat T Cells. X-axis: concentration of an antibody or an Fab fragment. Y-axis: mean fluorescence intensity (MFI). Samples F1-F6 represent Fab fragments, samples W1-W6 refer to whole antibodies. Mara-1 is a negative control murine IgG1.

The results are given in FIG. 2:

Legend of FIG. 2:
X-axis: antibody or Fab fragments concentration
Y-axis: mean fluorescence intensity (MFI)
—◇—: F1=Fab fragments of the antibody CD28.1
—■—: F2=Fab fragments of the antibody CD28.2
—▲—: F3=Fab fragments of the antibody CD28.3
—x—: F5=Fab fragments of the antibody CD28.5
—○—: F6=Fab fragments of the antibody CD28.6
••●••: W1=whole antibody CD28.1
••-••: W2=whole antibody CD28.2
—○—: W3=whole antibody CD28.3
—■—: W5=whole antibody CD28.5
—*—: W6=whole antibody CD28.6
—▲—: Mara-1=negative control (mouse IgG1).

These results show that, among the Fab fragments, only those derived from CD28.3 are capable of significantly binding to the CD28+ Jurkat cells at concentrations of less than 10 µg/ml.

2) Effect of the Fab Fragments on the Adhesion of CD28+ Jurkat T Cells to Transfected Murine L Cells Expressing the B7-1 Molecule:

$4\times10^5$ human T cells (Jurkat, CD28-positive) labeled with $^{51}Cr$ are incubated for 2 hours in a microtitration plate in which $10^5$ adherent $LTK^-$ or $LB7^+$ cells (murine fibroblasts transfected with human B7.1 [PAGES et al., J. Biol. Chem., 271, 9403, (1996)] have been seeded 24 hours beforehand. These incubations are carried out in the presence of the Fab fragments derived from the antibodies CD28.1 to CD28.6, or of the antibody CD28.3, diluted to various dilutions in PBS buffer without $Ca^{2+}$ or $Mg^{2+}$. The adherent cells after washing are quantified by reading the residual radioactivity in a beta counter (PACKARD TOPCOUNT).

Figure 3:
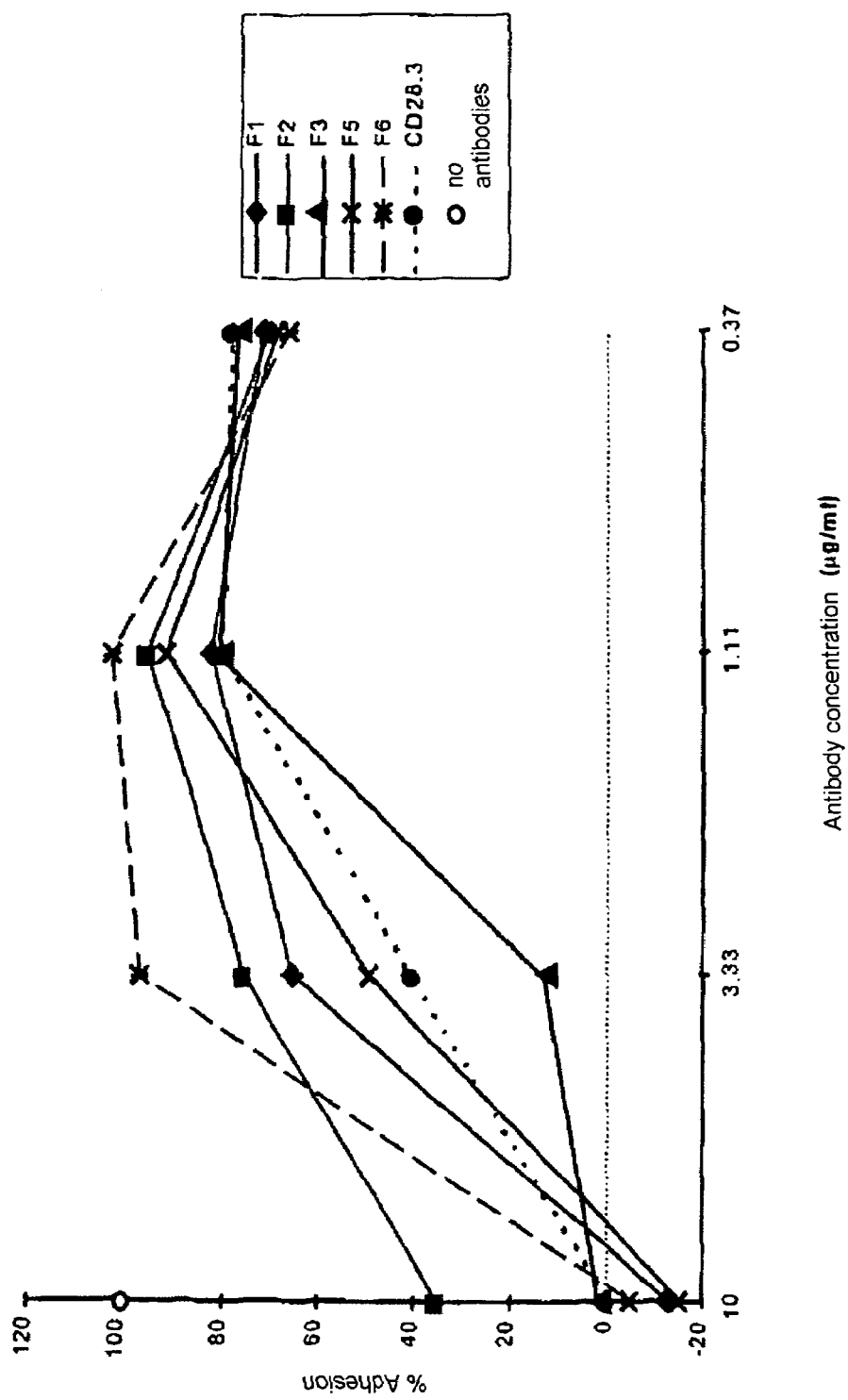
FIG. 3 shows the effect of the Fab fragments on the adhesion of CD28+Jurkat T cells to transfected murine L cells expressing the B7-1 molecule. X-axis: percentage of adherent cells. Y-axis: antibody concentration. Samples F1-F6 are Fab fragments which are presented along with results from whole antibody CD28.3 and a negative control (no antibody).

The results are given in FIG. 3:
Legend of FIG. 3:
X-axis: percentage of adherent cells
Y-axis: antibody concentration
—♦—: F1=Fab fragments of the antibody CD28.1
—■—: F2=Fab fragments of the antibody CD28.2
—▲—: F3=Fab fragments of the antibody CD28.3
—x—: F5=Fab fragments of the antibody CD28.5
—*—: F6=Fab fragments of the antibody CD28.6
••●••: whole antibody CD28.3
○: no antibody.

These results show that the Fab fragments derived from CD28.3 are the most effective for inhibiting CD28/B7 interactions. They give 90% inhibition of adhesion at a concentration of 3 μg/ml, and with an effectiveness comparable to that of the whole antibody CD28.3, whereas, at this concentration, the Fab fragments derived from the other antibodies give no more than 50% inhibition of adhesion.

3) Effect of the Fab Fragments on Proliferation in a Mixed Lymphocyte Reaction:

$10^5$ peripheral blood mononuclear cells (PBMCs) are mixed with $10^5$ allogenic mononuclear cells irradiated at 35 Gy, in the presence of varying concentrations of the antibodies CD28.1 to CD28.6 or of the Fab fragments derived from these antibodies. The proliferative response in these cultures is evaluated after 3 days, by incorporation of ($^3$H) thymidine for a period of 16 hours.

Figure 4:
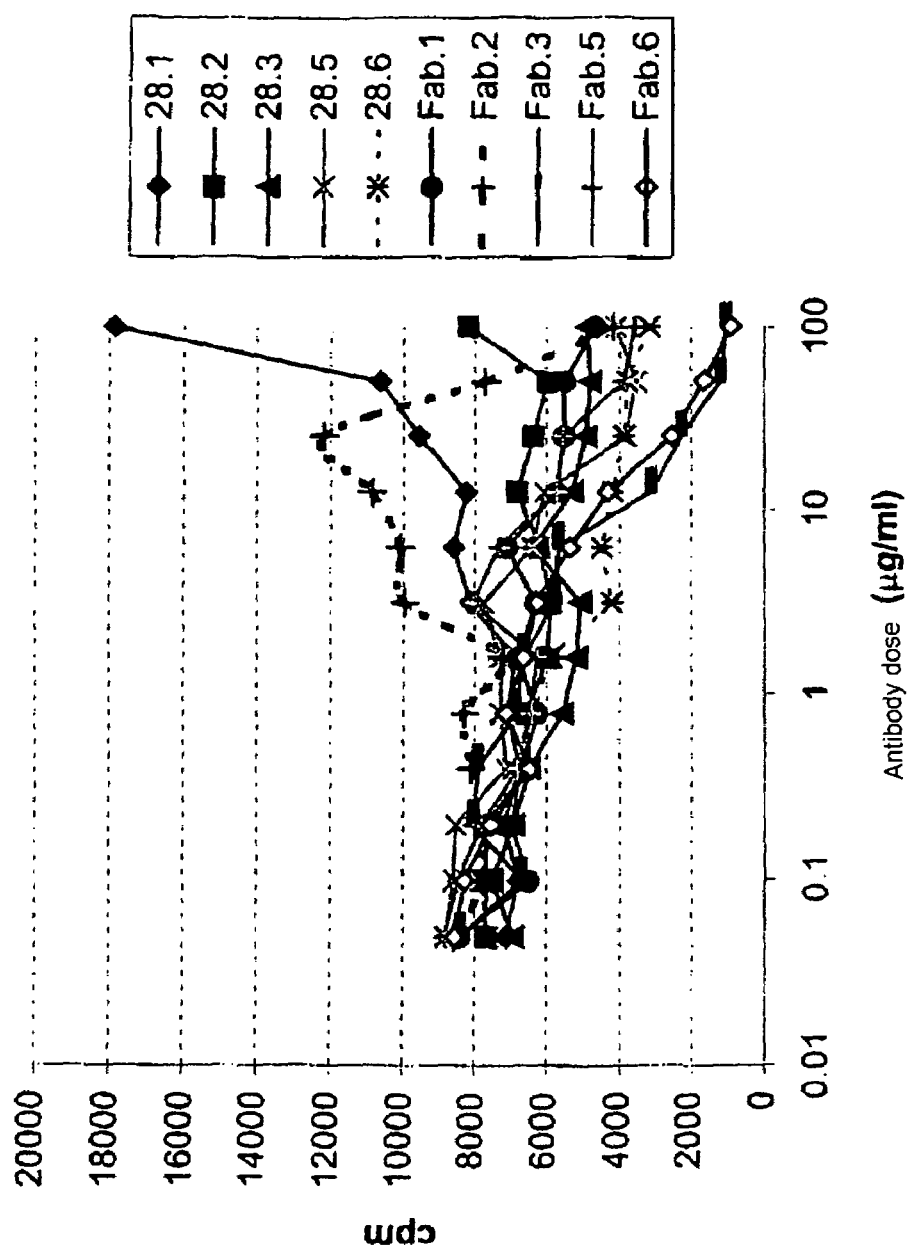
FIG. 4 shows the effect of the Fab fragments on proliferation in a mixed lymphocyte reaction. X-axis: antibody concentration and Y-axis: proliferative response (cpm). This figure compares data from live antibody samples and five Fab fragment samples.

The results are given in FIG. 4:
Legend of FIG. 4:
X-axis: antibody concentration
Y-axis: proliferative response (cpm)
Basal level of proliferation=6 500 cpm.
—♦—: 28.1=antibody CD28.1
—■—: 28.2=antibody CD28.2
—▲—: 28.3=antibody CD28.3
—x—: 28.5=antibody CD28.5
••—*•••: 28.6=antibody CD28.6
—●—: Fab. 1=Fab fragments of the antibody CD28.1
••+••: Fab. 2=Fab fragments of the antibody CD28.2
—■—: Fab. 3=Fab fragments of the antibody CD28.3
—+—: Fab. 5=Fab fragment of the antibody CD28.5
—◊—: Fab. 6=Fab fragment of the antibody CD28.6.

These results show that the Fab fragments derived from CD28.3 or from CD28.6 are the most effective for inhibiting mononuclear cell proliferation. The whole antibodies CD28.1 to CD28.6, tested in parallel, have no inhibitory effect or indeed stimulate the proliferation by virtue of their stimulator action on CD28.

Effect of the Fab Fragments Derived from CD28.3 on Proliferation Induced by a Superantigen For this experiment, responder CD4+ T cells were mixed with irradiated isogenic PBMCs, in the presence of 50 ng/ml of toxic shock syndrome toxin-1 (TSST-1), which specifically stimulates the vβ2+ T cell, either in the absence of antibody or in the presence of anti-B7-1 (1 μg/ml), of anti-B7-2 (0.5 μg/ml), of CTLA4Ig (10 μg/ml), or of Fab fragments derived from CD28.3 (10 μg/ml).

The proliferative response in these cultures is evaluated after 1, 3, 6 and 8 days, by incorporation of ($^3$H) thymidine for a period of 16 hours.

Figure 5:
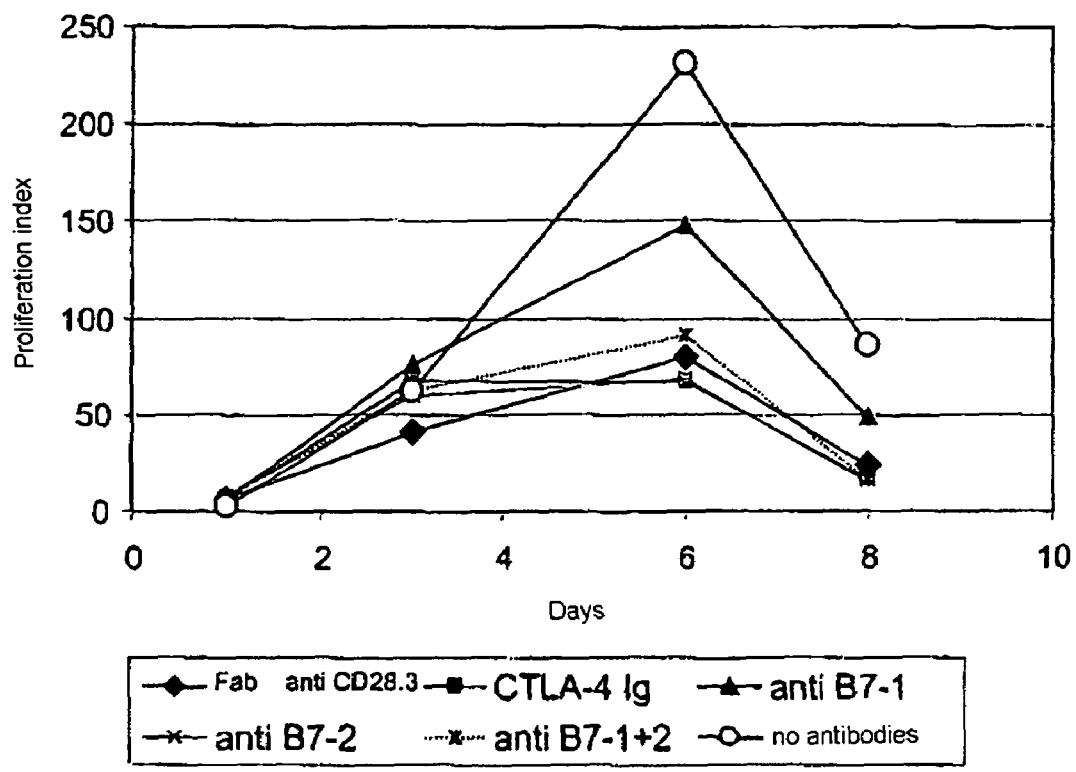
FIG. 5 shows the effect of the Fab fragments derived from CD28.3 on proliferation induced by a superantigen. X-axis: culturing time and Y-axis: proliferation index P1. The effects of anti-CD28.3 Fab are compared with those from anti-B7.2, CTLA-4 Ig, anti-B7-1+2, anti-B7-1 and with a negative control (no antibody).

The results are given in FIG. 5:
Legend of FIG. 5:
X-axis: culturing time
Y-axis: proliferation index=PI $$PI = \frac{cpm \text{ mixed lumphocyte reaction} - cpm \text{ irradiated stimulating cells only}}{cpm \text{ unstimulated responder cells}}$$

—♦—: anti-CD28.3 Fab
—X—: anti-B7-2
—■—: CTLA-4 Ig
••*••: anti-B7-1+2
—▲—: anti-B7-1
—○—: no antibody TSST-1 induces considerable proliferation of CD4+ T cells. In the presence of anti-B7, of CTLA4Ig or of the Fab fragments of CD28.3, 70% inhibition of this proliferation is observed after 6 days.

Effect of the Fab Fragments Derived from CD28.3 on Cytokine Production

In order to determine whether the Fab fragments derived from CD28.3 could induce an immune deviation in vitro, a mixed lymphocyte reaction (PBMCs derived from a donor A/irradiated PBMCs derived from a donor B) was carried out, in the presence of Fab fragments derived from CD28.3. $10^5$ peripheral blood mononuclear cells from a donor are mixed with $10^5$ allogenic mononuclear cells irradiated at 35 Gy, and cultured for 5 days in the presence or absence of 10 μg/ml of Fab derived from the antibody CD28.3.

The RNA of the responder cells was extracted, and the amount of cytokine mRNA was evaluated by quantitative measurement of the number of transcripts, related to the amount of HPRT, using a TaqMan (Perkin Elmer).

In the presence of Fab fragments derived from CD28.3, a decrease in the production of γIFN and of IL2, and an increase in the production of IL10 are observed. This deviation in the immune response suggests an orientation toward a Th2-type response. This result is unexpected insofar as it has been reported that the involvement of CTLA4 (which is supposed to intervene in the blocking of CD28 alone) leads to a Th1-type response.

In Vitro Processing of the Antibody CD28.3 and of the Fab Fragments Derived Therefrom, by Human T Cells A possible internalization of the Fab fragments of the antibody CD28.3 in human T cells was investigated, in comparison with the whole antibody CD28.3.

Jurkat T cells were incubated in culture medium with 100 μg/ml of antibody CD28.3, at 37° C. or at 0° C. At various times, the cells were washed with cold PBS buffer containing 0.1% of bovine serum albumin, and NaN$_3$, in order to block membrane motility. The bound antibodies were revealed with a fluorescein-labeled goat anti-mouse secondary antibody. The cells were mounted in MOVIOL and analyzed by confocal microscopy.

It is thus observed that the whole CD28.3 antibodies which bind to the Jurkat T cells are captured and disappear from the cell surface at 37° C., but not at 0° C. On the other hand, Fab fragments remain attached at the surface of the cell. This indicates that the attachment of the divalent antibodies CD28.3 leads to dimerization of CD28, which brings about

EXAMPLE 2

Properties of an scFv Fragment Derived from the Antibody CD28.3

FIG. 1 represents the polypeptide sequence of an scFv fragment derived from the antibody CD28.3. The portions of this sequence corresponding to the variable fragment of the heavy chain and of the light chain are represented in capital letters. The sequence corresponding to the variable fragment of the light chain is also underlined. The sequence of the linker is represented in italics. The sequences of the CDRs of the heavy chain and of the light chain are boxed in.

The nucleotide sequence encoding this scFv fragment is represented in the attached sequence listing, under the number SEQ ID No.1.

The cDNA encoding this scFv fragment was inserted into the vector pIG6 (Biochemisches Institut, University of Zurich). This vector comprises in particular an ampicillin resistance marker and an expression cassette which comprises an inducible lac promoter under the control of which are placed: a sequence encoding an ompA signal peptide, a sequence encoding a marker peptide of sequence (1-letter code) DYKD, a sequence encoding a c-myc marker peptide, and a sequence encoding a polyhistidine-5 marker.

The cDNA encoding the scFv fragment described above was introduced between the EcoRI and EcoRV sites of pIG6, downstream of the sequence encoding the peptide DYKD and upstream of the sequence encoding the c-myc marker.

The construct obtained is called pIg6-28.3.

Production in Prokaryotic Cells

The vector pIg6-28.3 was used to transform *E.coli* JM83 cells. The cells are cultured at 25° C., up to an $OD_{550}$ of 0.5. After induction with IPTG, the scFv fragment is produced in soluble form in the periplasma. After electrophoresis and Western blotting, it appears in the form of a band at approximately 30 kDa.

It is purified from the periplasmic extracts of the bacteria, obtained after osmotic shock in 50 mM Tris-Cl, and ultracentrifugation of the insoluble material, by chromatography on an Ni-NTA matrix and ion exchange on DEAE-Sepharose.

The binding of the scFv fragments present in the eluate of the NiNTA column, to CD28+ Jurkat cells, is comparable to that obtained with Fab fragments obtained from the antibody CD28.3 by digestion with papain.

Production in Eukaryotic Cells

The vector pSec-28.3 was used to transfect Cos cells. The cells are cultured at 37° C. for 3 days. The scFv fragment is produced in soluble form in the supernatant. This supernatant inhibits the mixed lymphocyte reaction: $10^5$ peripheral blood mononuclear cells from a healthy donor are mixed with $10^5$ peripheral blood mononuclear cells from another, healthy allogenic donor. The proliferative response in these cultures is evaluated after 5 days by incorporation of ($^3$H) thymidine for a period of 16 hours. Considerable inhibition of the incorporation, dependent on the supernatant dilution used, is observed. A control supernatant exhibits no proliferation-inhibiting activity.

EXAMPLE 3

Production of a Fusion Protein Comprising an scFv Fragment of CD28.3

The nucleotide sequence encoding the scfv fragment described in example 2 was linked to the 5' end of a portion of the cDNA of human α1-antitrypsin (GENBANK accession number K01396) corresponding to amino acids 53 to 425, via a hinged peptide of sequence VAAPS. The resulting sequence is represented in the attached sequence listing under the number SEQ ID No. 3, and the corresponding polypeptide under the number SEQ ID No. 4.

EXAMPLE 4

Construction of Expression Vectors Comprising the Sequence Encoding α1-Antitrypsin and Allowing the Introduction of a Sequence Encoding an scFv Fragment Prokaryotic Expression Vector:

The vector pIG6 was used (Biochemisches Institut, University of Zurich). This vector comprises in particular an ampicillin resistance marker, and an expression cassette which comprises an inducible lac promoter under the control of which are placed: a sequence encoding an ompA signal peptide, a sequence encoding a marker peptide of sequence (1-letter code) DYKD, a sequence encoding a c-myc marker peptide, and a sequence encoding a polyhistidine-5 marker.

The cDNA encoding a fragment of human α1-antitrypsin corresponding to amino acids 53 to 425 was introduced between the EcoRI and EcoRV sites of pIg6, downstream of the sequence encoding the peptide DYKD and upstream of the sequence encoding the c-myc marker.

The construct obtained, is called pIg6-Haat.

Eukaryotic Expression Vector:

The vector pSECTagB (Invitrogen, De Schelp, The Netherlands) was used. This vector comprises in particular an ampicillin resistance marker, a zeocin resistance marker, and an expression cassette which comprises a CMV promoter under the control of which are placed: a sequence encoding a signal peptide of the IgG kappa light chain, a sequence encoding a c-myc marker peptide, and a sequence encoding a polyhistidine-6 marker.

The cDNA encoding a fragment of human α1-antitrypsin corresponding to amino acids 53 to 425 was introduced between the BamHI and EcoRI sites of the vector PSEC B Tag, upstream of the sequence encoding the c-myc marker.

The construct obtained is called pSecHaat.

EXAMPLE 5

Construction of Expression Vectors Integrating the Sequence Encoding the CD28.3 scFv/α1-Antitrypsin Fusion Protein Prokaryotic Expression Vector:

The cDNA encoding the CD28.3 ScFv/α1-antitrypsin fusion protein described in example 3 above was introduced between the EcoRI and XhoI sites of pIG6, downstream of the sequence encoding the peptide DYKD and upstream of the sequence encoding the c-myc marker.

The construct obtained is called pIg6Haat.

Eukaryotic Expression Vector:

The cDNA encoding the CD28.3 ScFv/α1-antitrypsin fusion protein described in example 3 above was introduced between the BamHI and XhoI sites of the vector PSEC B Tag, upstream of the sequence encoding the c-myc marker.

The construct obtained is called pSecHaat.

This vector, harbored by *E.coli* DH5α, was deposited with the CNCM on Dec. 11, 2001, under the number I-2762.

EXAMPLE 6

Expression and Purification of the Fusion Proteins

In Prokaryotic Cells:

The vector pIg6-28.3Haat was used to transform *E. coli* JM83 cells. The cells are cultured at 25° C., up to an $OD_{550}$ of 0.5. After induction with IPTG, the protein is produced in soluble form in the periplasm. After electrophoresis and Western blotting, it appears in the form of a band at approximately 74 kDa.

It can be purified from the periplasmic extracts using an NI-NTA affinity chromatography matrix and/or an anti-c-myc affinity chromatography matrix. It can also be purified using an anti-α1-antitrypsin affinity column.

In Eukaryotic Cells:

The vector pSec-28.3Haat was used to transfect CHO cells by lipofection. The cells are cultured in the presence of 200 µg/ml on zeocin in MEM medium containing 10% of fetal calf serum.

The protein is secreted into the culture medium.

After separation by electrophoresis, Western blotting, and revelation with an anti-c-myc antibody, it appears in the form of a band at approximately 80 kDa.

EXAMPLE 7

Assays for Activity of an scFv/α1-Antitrypsin Fusion Protein

The anti-CD28 activity of the CD28.3 scFv/α1-antitrypsin fusion protein obtained in example 6 above was evaluated by its binding to the CD28 molecule, or to cells expressing CD28 on their membrane, and its lack of binding to cells which do not express CD28.

The immunosuppressor activity of the CD28.3 scFv/α1-antitrypsin fusion protein obtained in example 6 above is evaluated by the inhibition of adhesion to B7, and the inhibition of the induced activation of the T lymphocyte.

These anti-CD28 and immunosuppresor activities were measured using the following assays:

Anti-CD28 Activity

Biosensor Measurement of the CD28-Binding Parameters:

Recombinant human CD28 was immobilized on the biosensor (BIACORE) detector. A CD28.3 scFv/α1-antitrypsin fusion protein obtained as described in example 6 above was brought into contact with the detector. The binding parameters are: KA (1/M)$2.86^e 9$; KD (M): $3.49^e$-10. In comparison, these parameters measured for the Fab fragment of the antibody CD28.3 are: KA (1/M): $9.69^e 8$; KD (M): $1.03^e$-9. The affinity for CD28, of the Fab fragment of the antibody CD28.3 and of the fusion protein, are therefore comparable.

Cytofluorometry Assay for Specific Recognition of CD28:

$10^5$ Jurkat (Cd28+) and U937 (CD28−) cells are incubated in PBS-1% BSA-0.1% $NaN_3$, at 4° C., for 1 hour with increasing concentrations of the CD28.3 scFv/α1-antitrypsin fusion protein. After washing, the cells are incubated with an anti-alpha-1-antitrypsin rabbit antibody and then with an FITC-conjugated goat anti-rabbit antibody, washed, and analyzed by cytofluorometry. Binding dependent on the dose of the Jurkat cells (CD28+), and no binding to the U937 (CD28−) cells, were observed. This shows the specificity of the fusion protein for the CD28 molecule and its lack of reactivity toward other molecules expressed by human hematopoietic cells.

Immunosuppressor Activity

CD28/B7-Dependent Adhesion Assay:

$4 \times 10^5$ human T cells (CD28-positive Jurkat cells) labeled with $^{51}Cr$ are incubated for 2 hours in a microtitration plate in which $10^5$ adherent $LTK^-$ or $LB7^+$ cells (murine fibroblasts transfected with human B7.1 [PAGES et al., J. Biol. Chem., 271, 9403 (1996)] had been seeded 24 hours beforehand. These incubations are carried out in the absence or in the presence of the CD28.3 scFv/α1-antitrypsin fusion protein, diluted to various concentrations in PBS buffer without $Ca^{2+}$ or $Mg^{2+}$. The adherent cells after washing are quantified by reading the residual radioactivity using a beta counter (PACKARD TOPCOUNT). Inhibition of the adhesion in the presence of the CD28.3 scFv/α1-antitrypsin fusion protein is observed, which inhibition is directly dependent on the dose of fusion protein used.

Inhibition of the Activation:

$5 \times 10^4$ T cells (human polyclonal cells depleted of CD11b cells) are stimulated with $1 \times 10^4$ irradiated OKT3 hybridoma cells (anti-CD3), or with allogenic $CD28^-$ B cells (depleted of $CD28^+$ cells), in the absence or in the presence of varying amounts of the CD28.3 scFv/α1-antitrypsin fusion protein. The proliferative response in these cultures is evaluated after 3 days when the stimulation is performed with anti-CD3s, or after 7 days when the stimulation is performed with allogenic cells, by incorporation of ($^3H$) thymidine for a period of 16 hours. Considerable inhibition of the incorporation is observed in the presence of the CD28.3 scFv/α1-antitrypsin fusion protein, which inhibition is directly dependent on the dose of fusion protein used.

Inhibition of the Mixed Lymphocyte Reaction:

$10^5$ peripheral blood mononuclear cells from a healthy donor are mixed with $10^5$ peripheral blood mononuclear cells from another, allogenic, healthy donor. The proliferative response in these cultures is evaluated after 5 days by incorporation of ($^3H$) thymidine for a period of 16 hours. Considerable inhibition of the incorporation is observed in the presence of the CD28.3 scFv/α1-antitrypsin fusion protein, which inhibition is directly dependent on the dose of fusion protein used.

The invention claimed is:

1. A protein comprising the complementarity determining regions (CDRs) of immunoglobulin CD28.3, which is an immunoglobulin produced by hybridoma CNCM I-2582;
   wherein said CDRs are CDR1, CDR2 and CDR3 of the light chain of CD28.3 and CDR1, CDR2, and CDR3 of the heavy chain of CD28.3.

2. The protein of claim 1 that is an antibody or a fragment thereof comprising the CDRs of immunoglobulin CD28.3.

3. The protein of claim 1 that is antibody CD28.3 that is produced by the hybridoma cell line deposited as CNCM I-2582, or a fragment thereof comprising the CDRs of immunoglobulin CD28.3.

4. The protein of claim 1 that is an Fab, Fab'2, Fv, or scFv antibody fragment comprising the CDRs of immunoglobulin CD28.3.

5. The protein of claim 1 that is a humanized or chimeric antibody or a fragment thereof comprising the CDRs of immunoglobulin CD28.3.

6. The protein of claim 1 that is a recombinant antibody.

7. The protein of claim 1 that is encoded by the plasmid deposited as CNCM I-2762.

8. The protein of claim 1 that is monovalent, having only one binding site for CD28.

9. The protein of claim 8 that inhibits the interaction between CD28 on a lymphocyte and B7-1 or B7-2 on an antigen presenting cell.

10. The protein of claim 1 that is plurivalent, having more than one binding site for CD28.

11. The protein of claim 10 that induces the dimerization of CD28 on a lymphocyte.

12. A composition comprising the protein of claim 1.

13. The composition of claim 12 in a form suitable for medicinal or pharmaceutical use or in a form suitable for in vivo administration.

14. The composition of claim 12 in a form suitable for diagnostic use.

15. A method for activating T lymphocytes in a subject comprising administering to a subject in need thereof an effective amount of the protein of claim 10.

* * * * *